United States Patent [19]

Sheffield

[11] Patent Number: 5,057,494

[45] Date of Patent: Oct. 15, 1991

[54] METHOD FOR PREVENTING TISSUE DAMAGE AFTER AN ISCHEMIC EPISODE

[75] Inventor: Warren D. Sheffield, Lebanon, N.J.

[73] Assignee: Ethicon, Inc., Somerville, N.J.

[21] Appl. No.: 227,579

[22] Filed: Aug. 3, 1988

[51] Int. Cl.[5] .................... A61K 37/02; A61K 37/36
[52] U.S. Cl. .................................. 514/12; 514/21
[58] Field of Search ................................. 514/12, 21

[56] References Cited

U.S. PATENT DOCUMENTS 4,378,347  3/1983  Franco ................................ 514/777
4,845,075  7/1989  Murray .............................. 530/350

FOREIGN PATENT DOCUMENTS

0138572A2  4/1985  European Pat. Off. .

Primary Examiner—F. T. Moezie
Attorney, Agent, or Firm—Richard J. Grochala

[57] ABSTRACT

A method is provided for preventing tissue damage in a patient after the tissue has been deprived of blood supply resulting in ischemia. The method involves administering to the patient a polypeptide having epidermal growth factor activity or fibroblast growth factor activity prior to or after the ischemic event.

10 Claims, No Drawings

METHOD FOR PREVENTING TISSUE DAMAGE AFTER AN ISCHEMIC EPISODE

BACKGROUND OF THE INVENTION

The present invention concerns the use of epidermal growth factor (EGF) and fibroblast growth factor (FGF) in methods for preventing tissue damage in a patient after the tissue has been deprived of its blood supply, for example as occurs after an ischemic episode.

Many tissues of the body are highly susceptible to tissue damage or death following a period of inadequate oxygen and nutrient supply, as occurs when there is an insufficiency of arterial blood supply or venous drainage. In such cases, an infarct may develop in the tissue, which is an area of necrosis resulting from the sudden reduction of the blood supply. A reduction in the blood supply to a tissue may be caused by blockage of a vein or artery servicing that tissue. Such a blockage of the blood supply may be caused by emboli or thrombi (types of blood vessel clots), vascular torsion or pressure that produces a macroscopic area of necrosis. Tissues that are likely to be affected by a reduction of blood supply and oxygen are central nervous system (CNS), myocardial, renal, spleen, intestinal and lung tissues.

A sudden reduction in the blood supply to a tissue is generally referred to as an ischemic event and as used herein the term "ischemic" shall mean a local anemia due to an obstruction (of any type) of the blood supply to that tissue (usually by arterial narrowing). Common examples of this type of problem are myocardial ischemia, which is the inadequate circulation of blood to myocardium, usually as a result of coronary artery disease; myocardial infarction, which is an infarction of an area of the heart muscle usually as a result of occlusion of a coronary artery; and cerebral ischemia or stroke, which is a neurological affliction resulting from the sudden reduction in cerebral blood supply. The term "stroke" (sometimes called apoplexy) is a lay term which refers to the sudden diminution or loss of consciousness, sensation and voluntary motion caused by rupture or obstruction of an artery of the brain. Stroke is usually more specifically described by the nature of the underlying disturbance, e.g. thrombosis, hemorrhage or embolism.

Cerebral ischemia may be distiguished from hypoxia, which is the interference with the oxygen supply to the brain despite a relatively normal cerebral blood flow and normal perfusion pressure. Cerebral hypoxia occurs for a variety of reasons, including a general reduction of atmospheric oxygen tension, pollution of the atmosphere (e.g., by carbon monoxide), chronic Pulmonary disease, pulmonary emboli and reduced or altered oxygen-carrying capability of the blood (e.g., anemia). Ischemic infarction will occur as a consequence of severe hypoxia.

There are various degrees of cerebral ischemia. A transient ischemic attack (TIA) is defined as a loss of neurologic function caused by ischemia, abrupt in onset, persisting for less than twenty-four hours, and clearing without residual signs. Most such TIA's last only a few minutes. If disability persists for more than twenty-four hours, but is attended ultimately by no persisting symptoms or signs, it is conventionally called a reversible ischemic neurologic disability (RIND). An ischemic event that is sufficiently severe and in an appropriate location to leave persistent disability but is short of a calamatous stroke, is defined as a partial nonprogressing stroke (PNS). The ultimate in severity of ischemia produces a more major degree of permanent neurologic disability, sometimes referred to as a completed stroke. In those cases where the ischemia has been prolonged, neuronal cell death occurs. The brain softens and the margins between the gray and white matter become indistinct. Under the microscope the neurons (if still present) may be observed to be shrunken and pyknotic. These lesions result in permanent neurologic disability.

Present therapies for treating or preventing ischemic events, such as cerebral stroke, include risk factor management, anti-spasmodic drugs, anti-thrombotic drugs and surgery. These therapies have disadvantages and are not always successful. Therefore, the medical community is in need of a better method for treating or preventing ischemic events. The present invention provides such methods by use of EGF and FGF to treat the damaged tissue. At the present time, there are no clinically useful methods for the direct protection of neurons and/or glia cells (aka neuroglia cells, which are non-neuronal cellular elements of the central and peripheral nervous systems) following cerebral ischemia and the present invention provides such methods.

To date, nerve growth factor (NGF) is the most well known polypeptide cell growth factor whose presence has been demonstrated to be unequivocally required for maintenance and maturation of neuronal cells. Most of the other polypeptide cell growth factors do not have the same effect on neuronal cells. For instance, in the past, EGF has not been shown to have an effect on neuronal growth and it does not bear any structural similarity to NGF.

Furthermore, there is no sequence homology between NGF and EGF and neither growth factor can compete with the homologous ligand-receptor interaction of the other growth factor.

Fibroblast growth factor, on the other hand, is known to be neurotrophic (i.e., stimulates the growth of neuronal cells). For example, see Unsicker, K. et al., Proc. Natl. Acad. Sci. USA 84:5459-5463 (August 1987); Gensburger, C. et al., FEBS Lett. 217:1-5 (June 1987); Siebers, J. et al., Neuroscience Letters 76:157-162 (1987); and Morrison, R.S., J. Neurosci. Res. 17:99-101 (1987). Also, FGF has been described as useful to treat heart disease. See, U.S. Pat. Nos. 4,296,100 and 4,378,347 which both describe the use of fibroblast growth factor in the treatment of ischemic heart disease and myocardial infarction. In a recent publication, Anderson et al. (Nature 332:360-361 (March 24, 1988)) describe that FGF may be beneficial in the treatment of Alzheimer's disease as well as treatment of other neurodegenerative disorders of the CNS involving loss of non-cholinerigic neurons such as stroke, epilepsy or ischemia. In spite of the known neurotrophic nature of FGF, prior to the present invention, no one has suggested its use to prevent tissue damage after an ischemic event has occurred.

SUMMARY OF THE INVENTION

The present invention provides methods for prevent tissue damage in a patient after the tissue has been deprived of blood supply for a tissue damaging amount of time. The methods comprise administering to the patient a polypeptide having epidermal growth factor activity so as to contact the ischemic tissue therewith. The growth factor may be used alone or in combination with other growth factors, such as FGF, NGF, platelet-derived growth factor, insulin-like growth factor or transforming growth factor (alpha or beta). The EGF may be administered to the patient separately or in combination with one or more of a free radical scavenger material, such as superoxide dismutase; or a fibrinolytic agent, such as a plasminogen activator. The EGF may be administered to the patient prior to or after ischemia.

DETAILED DESCRIPTION OF THE INVENTION

One of the better characterized growth factors is epidermal growth factor. Human EGF is a fifty-three amino acid polypeptide growth factor that has mitogenic activity for a number of kinds of cells, including epithelial and mesenchymal cells. Variants of the naturally occuring EGF molecule have been reported, such as the fifty-two amino acid gamma-urogastrone. EGF has also been reported to have angiogenic activity. Epidermal growth factor exhibits epidermal growth promoting activity and gastric acid secretion inhibiting activity, and is therefore useful as a medicament. A review of epidermal growth factor can be found in Carpenter, G. et al., "Epidermal Growth Factor, Its receptor, and Related Proteins," Exp. Cell Res. 164:1-10 (1986). Human EGF refers to EGF having that polypeptide sequence or any substantial portion thereof as set forth in Urdea M.S. et al., Proc. Natl. Acad Sci. U.S.A. 80:6461-6465 (1983). Human EGF also refers to any naturally occurring human EGF variant such as gamma-urogastrone.

Epidermal growth factor, including human EGF, may be isolated from natural sources, produced using recombinant DNA techniques or prepared by chemical synthesis. It is contemplated that biologically active fragments or chemically synthesized derivatives of EGF may be used in the present methods instead of the entire naturally occurring molecule, provided that such fragments or derivatives retain the biological activity of naturally occurring EGF. As used herein, EGF includes the EGF produced by recombinant DNA techniques, mouse EGF isolated from the submaxillary glands of mice, rat EGF and natural human EGF, which may be isolated from human urine, and bioactive derivatives and related polypeptides of any of the foregoing, including precursors that are transformed into active EGF in situ by proteolytic processing. As used herein, the phrase "polypeptide having epidermal growth factor activity" includes any bioactive analog, fragment or derivative of the naturally occurring EGF molecule.

FGF has been described in International Patent Application Publication No. WO 87/01728. This publication sets forth the amino acid sequences of acidic and basic FGF as well as recombinant methods of producing these molecules. As used herein, FGF refers to either acidic or basic FGF, as well as any bioactive fragments or derivatives thereof. The phrase "polypeptide having fibroblast growth factor activity" includes any bioactive analog, fragment or derivative of the naturally occurring FGF molecule.

The term "analog" of a polypeptide refers to any polypeptide having a substantially identical amino acid sequence to that polypeptide in which one or more amino acids have been substituted with chemically similar amino acids. The term "analog" shall also include any polypeptide which has one or more amino acids deleted from or added to the polypeptide, but which still retains a substantial amino acid sequence homology to the polypeptide. A substantial sequence homology is any homology greater than 50%. The term "fragment" of a polypeptide refers to any shorter version of the polypeptide, having at least ten amino acid residues and having the same bioactivity as the polypeptide. The term "chemical derivative" refers to any polypeptide derived from EGF or FGF and in which one or more amino acids have been chemically derivatized synthetically by reaction of functional side groups of the amino acids (i.e. it is derived from EGF or FGF by one or more steps).

The EGF and FGF used in the present methods may be administered to the patient in the form of a pharmaceutical composition, wherein the EGF or FGF is admixed with a pharmaceutically acceptable carrier. The carrier may take a wide variety of forms depending on the form of preparation desired for administration, e.g. sublingual, rectal, nasal, intraventricular, intracerebral, oral or parenteral. If the compositions are to be injected directly into the patient's spinal cord, the carrier may be an artificial cerebrospinal fluid. Controlled release formulations may also be used.

For pharmaceutical compositions to be administered parenterally, the carrier will usually comprise sterile water, although other ingredients to aid solubility, buffering or for preservation purposes may be included. Also, extenders may be added to compositions which are to be lyophilized. Injectable suspensions may also be prepared, in which case appropriate liquid carriers, suspending agents and the like may be employed. Examples of parenteral routes of administration are intravenous, intraperitoneal, intramuscular or subcutaneous injection.

According to the present invention, EGF or FGF may be used in methods for preventing tissue damage in a patient after the tissue has been ischemic for a tissue damaging amount of time. The methods comprise administering to the patient EGF or FGF or a polypeptide having EGF or FGF activity so as to contact the ischemic tissue therewith. As used herein, "tissue damaging amount of time" means an amount of time in which the tissue cells are deprived of blood supply and are either damaged or killed by ischemia and is generally in the range of 2-5 minutes. In one embodiment, the present methods may be used to treat neuronal or CNS tissue, such as is present in the brain and spinal cord of the CNS. It is envisioned that the present methods may also be useful for treating other types of tissues such as myocardial tissue, renal tissue, spleen tissue, intestinal tissue, and lung tissue, which may also be damaged after an ischemic episode.

The EGF and FGF may be administered to the tissue to be treated in the patient (such as a human) in any manner which brings the EGF into contact with the tissue. Administration is preferred to be as soon after injury as feasible. Preferably, the EGF or FGF is administered parenterally and most preferably by intravenous injection. The EGF or FGF may also be administered in the form of a sterile implant for Prolonged action.

In those instances where CNS tissue is to be treated, direct injection into the CNS is preferred, such as by intracerebral or intraventricular injection or by injection into the cerebro- spinal fluid or spinal cord. For injection into the CNS, catheters, needles and syringes may be used. Infusion of the EGF or FGF via a catheter into the brain is an alternative method of administration.

An example of a dosing regimen for a post-ischemic patient involves a bolus injection of the EGF or FGF followed by continuous infusion. Also, a sustained release dose or repeated delivery of the drug may be used. An example of a dosing regimen for a pre-ischemic patient (e.g., prior to a transplant) may be a continuous infusion of drug.

EGF or FGF may also be used in a method for preventing permanent tissue damage in a patient from ischemia by administering the EGF or FGF to the patient prior to the ischemic episode. Such a preventative method may be used in those cases when blood supply will be reduced to a specific organ, for example because of surgical procedures. It also may be used in those patients who are susceptible or known to be susceptible to having an ischemic episode, such as high risk or TIA patients or to prevent reoccurrance after a first ischemic event.

Thus, the present methods may be used in a variety of indications. A few examples of such indications are set forth merely for illustrative Purposes. For instance, the present methods may be used to minimize damage and increase survival time in stroke patients. They may be used as a preventative treatment of TIA patients to reduce subsequent serious stroke and increase patient and cell survival. They may be used to reduce risk for spinal ischemia and in cases of damage to the spinal cord, such as spinal cord compression associated with trauma. They may be used to lengthen the time available during surgery when aortic clamping is used. The present invention may be used to treat indications affecting the brain, such as stroke, cardiac arrest and post-resuscitation damage to the brain (e.g., from drowning or subarachnoidal hemorrhage). Indications affecting the heart that may be treated are, for example: post myocardial infarct recovery, prevention of reperfusion injury following thrombolytic therapy and/or angioplasty, and reperfusion arrhythmias. Indications affecting the kidney that may be treated include as examples: organ removal, storage and transplantation; and reperfusion damage.

A present concern in treating tissues that have been deprived of blood supply for a period of time is that reperfusion of the tissue with blood may result in damage to the tissue because of the production of oxygen free radicals. In such cases, means for destroying or counteracting the free radicals may help to minimize the extent of permanent damage to the tissue and thereby improve therapy for the patient. The superoxide derived radical is the usual free radical produced by cellular oxidation reactions, although its effects can be magnified because superoxide produces other kinds of cell-damaging free radical's and oxidizing agents. The therapies now being tested in the medical community use two different enzymes that normally help to protect cells against the free radical's effects. Superoxide dismutase (SOD) converts the free radical to hydrogen peroxide, which is then converted by catalase to water and molecular oxygen. Thus, the present invention contemplates the use of a free radical scavenger material, such as superoxide dismutase, in conjunction with catalase, to be used either prior to or simultaneously with EGF or FGF administration. Other substances which may be useful as free radical scavenging materials are vitamin E, beta-carotene, BHT and ascorbic acid (vitamin C), which are known to counteract oxygen radical formation. Additionally, iron chelator compounds may be useful to counteract the effects of free radicals.

Another problem that may be encountered in treating a tissue after an ischemic episode, is that one or more blood vessels supplying the tissue with blood may be blocked by a clot. Such a blockage may be removed mechanically, such as in coronary angioplasty in which an instrument (such as a small balloon which can be inflated) is inserted in a blocked artery to remove the blockage. Alternatively, the blockage may be removed chemically by the use of fibrinolytic agents, such as the class of enzymes referred to as plasminogen activators, which include streptokinase, urokinase and tissue plasminogen activator. Thus, the present invention also contemplates the use of a fibrinolytic agent, either prior to or simultaneously with the EGF or FGF administration to treat the blood deprived tissue.

As is readily apparent, any combination of EGF, free radical scavenger material or fibrinolytic agent and any combination of dosage regimen may be used within the scope of the present invention. For example, prior to EGF or FGF administration, a fibrinolytic agent may first be administered to the patient in order to open any blocked blood vessels. Then, SOD, alone or in combination with the EGF or FGF, may be administered to prevent reperfusion damage. Finally, the EGF or FGF may be administered to the patient. As previously mentioned, the EGF or FGF may be combined with other growth factors in the form of a "cocktail".

The following examples are presented to illustrate the subject invention The invention is not to be considered limited by this example but only by the appended claims.

EXAMPLE 1

The present example is based on a surgical procedure that has been developed to study the effects of cerebral or brain ischemia in the unanesthetized gerbil. The methodology is based upon the surgical isolation and instrumentation of both common carotid arteries. A loop of dental floss is placed around each carotid artery and passed through a double lumen catheter material; this allows for later occlusion of the carotid arteries and their release in the unanesthetized subject. Functional changes following transient carotid artery occlusion are readily demonstrated by the occurrence of altered spontaneous locomotor activity at various times postischemia. Behavioral changes consequent to stroke are useful and pertinent as a means of evaluation in this model of nonlethal transient ischemia Emotional lability, depression, agitation and motor and cognitive deficits are common after stroke. The psychomotor depression noted immediately after transient ischemia in this gerbil model mimics the clinical situation in humans. Spontaneous motor activity is an indicator of aroused state and is a behavior commonly measured in psychopharmacology research. Changes in locomotor activity have been shown in extensive pharmacological and toxicology studies to provide reliable, reproducible first-assessment data about neurological status. The details of this method are more fully set forth in Chandler, M.J. et al., J. Pharm. Meth. 14:137–146 (1985).

Ligatures externalized through double lumen catheters were surgically placed around both common carotid arteries of mature (50–60 gram) gerbils. After allowing recovery from surgery, conscious gerbils were subjected to a 5 minute period of bilateral carotid occlusion by tightening the ligatures. Spontaneous motor activity was then periodically monitered over seven days followed by animal sacrifice and blinded histological evaluation of brain sections. EGF (0.1 and 1.0 mg/kg) and FGF (0.1, 1.0 and 10.0 mg/kg) were given intraperitoneally in saline at one hour pre-occlusion and one, three, five and seven hours post-occlusion. Two control groups (occluded and non-occluded) received saline by the same route. At 1 mg/kg, EGF afforded almost total protection to the animal's neurons, as monitored either by motor activity (Table 1) or histology (Table 3). 0.1 mg/kg EGF produced a modest protection. FGF effectively protected neuronal cells at 0.1 mg/kg, but was ineffective at the higher doses (Tables 2 and 3). An explanation of the damage scoring system used for Table 3 is given in Table Spontaneous locomotor activity was recorded using photocell activity chambers. The chambers were two-foot circular arenas that were individually housed in sound attenuating compartments ventilated by a fan. Activity was monitored by two orthogonally placed photocell circuits. A single break of the photocell light beam by the animal's movements defined an activity count counts were monitored and recorded as a function of time. The data in Tables 1 and 2 represent activity counts.

It is not known how the EGF or FGF provided the protection observed. Without wishing to be bound by any particular theory, the possible explanations include: the enhanced survival of mitogenicly active versus quiescent cells; reduction of excitatory amino acid levels (e.g., glutamate which is known to cause hippocampal cell death) either by alternating production or stimulating glial-cell uptake; and reduction of free radical generation through effects on the producing cells.

EXAMPLE 2

Gerbils were treated as in Example 1, except that dosing was at 1,3,5 and 7 hours post-occlusion only. The results are set forth in Table 5.

Throughout this disclosure, various publications, patents and patent applications are referenced. The disclosures of these publications, patents and applications in their entireties are hereby incorporated by reference into this disclosure in order to more fully describe the state-of-the-art as known to those skilled therein as of the date of the invention described and claimed herein.

TABLE 1

EFFECTS OF EGF ON ISCHEMIA-INDUCED ALTERATION IN SPONTANEOUS LOCOMOTOR ACTIVITY IN GERBILS*

| TREATMENT | TIME AFTER ISCHEMIA (HRS) | | | | | |
|---|---|---|---|---|---|---|
| | 6 | 24 | 48 | 72 | 96 | 120 |
| SALINE (non-ischemic) | 485** (95) | 529 (101) | 613 (131) | 579 (133) | 493 (105) | 463 (89) |
| SALINE (post-ischemic) | 2366 (613) | 1960 (491) | 2145 (273) | 1011 (251) | 895 (153) | 486 (270) |
| EGF | | | | | | |
| 0.1 MG/KG | 1511 (186) | 658 (132) | 687 (150) | 715 (103) | 626 (106) | 511 (98) |
| 1.0 MG/KG | 705 (141) | 766 (153) | 588 (86) | 463 (56) | 445 (88) | 314 (47) |

*Gerbils were exposed to a 5-min period of bilateral carotid occlusion.
**Data represents the mean (+/− S.E.) of 6 gerbils per group.

TABLE 2

EFFECTS OF FGF ON ISCHEMIA-INDUCED ALTERATIONS IN SPONTANEOUS LOCOMOTOR ACTIVITY IN GERBILS*

| TREATMENT | TIME AFTER ISCHEMIA (HRS) | | | | | |
|---|---|---|---|---|---|---|
| | 6 | 24 | 48 | 72 | 96 | 120 |
| SALINE | (581) | 2315** (619) | 2819 (493) | 2351 (513) | 1917 (479) | 1553 (307) | 989 |
| FGF | | | | | | |
| 0.1 MG/KG | (128) | 583 (139) | 424 (121) | 611 (107) | 573 (137) | 591 (103) | 563 |
| 1.0 MG/KG | (483) | 2155 (481) | 1955 (418) | 2025 (426) | 1899 (366) | 1530 (317) | 1221 |
| 10.0 MG/KG | (324) | 2845 (358) | 2633 (406) | 1859 (494) | 1463 (389) | 1518 (332) | 1430 |

*Gerbils were exposed to a 5-min period of bilateral carotid occlusion
**Data represent the mean (+/− S.E.) of 6 gerbils per group

TABLE 3

EFFECTS OF EGF AND FGF ON ISCHEMIA-INDUCED DAMAGE TO THE HIPPOCAMPAL PYRAMIDAL CELL LAYER

| TREATMENT | EXTENT OF DAMAGE |
|---|---|
| NON-ISCHEMIC | 0, 0, 0, 0, 0, 0 |
| SALINE (ISCHEMIA) | 4, 4, 5, 5, 5, 4 |
| EGF 0.1 MG/KG | 3, 4, 3, 2, 3, 3 |
| EGF 1.0 MG/KG | 1, 0, 0, 0, 1, 0 |
| FGF 0.1 MG/KG | 2, 3, 2, 1, 2, 1 |
| FGF 1.0 MG/KG | 4, 5, 5, 4, 5, 5 |
| FGF 10.0 MG/KG | 4, 5, 5, 5, 5, 5 |

TABLE 4

| SCORE | CHARACTERISTICS |
|---|---|
| 0 | Normal cell distribution and no deposition of karyorectic material (degeneration of nuclear material). |
| 1 | Isolated cell loss at the borders of the hippocampus and slight degree of cell lysis and karyorectic material in the areas of cell lysis. |
| 2 | Modest number of necrotic foci in the dorsal hippocampus. Associated with the foci are substantial amount of karyorectic material in the dorsal (CA-1) hippocampus. |
| 3 | Multiple confluent foci of necrotic cells separated by a limited number of normal cells in the CA-1 region. These area of necrosis also contain a substantial amount of karyorectic material. |
| 4 | Severe confluent necrosis that extends to the limit of the CA-1 and into the CA-2 region. All surviving neurons in these necrotic areas are abnormal, no evidence of normal cells in these areas. |
| 5 | Complete loss of neurons in both the CA-1 and partial damage to the CA-3 pyramidal cells with partial necrosis in the CA-2 region. |

TABLE 5

| Treatment | Motor Activity at 24 hours | Average Histopathology Score |
|---|---|---|
| Saline | 3028 (281) | 4.8 |
| EGF 1 MG/KG i.p. | 715 (368) | 2.2* |
| EGF 0.1 MG/KG i.p. | 1051 (235) | 1.5* |
| EGF 0.01 MG/KG i.p. | 1891 | 4.7* |

TABLE 5-continued

| Treatment | Motor Activity at 24 hours | Average Histopathology Score |
|---|---|---|
| | (368) | |

Treatment effects were significant by one-way ANOVA ($p < 0.01$) for both motor activity and histopathology. Asterisk (*) denotes $p < 0.05$ relative to saline using Dunnett's multiple t-test.

The invention has been described herein with reference to certain preferred embodiments and examples. Since obvious variations will appear to those skilled in the art the invention is not to be considered limited thereto but only by the claims which follow.

What is claimed is:

1. A method for preventing tissue damage in a patient after the tissue has been deprived of blood supply for a tissue damaging amount of time, comprising administering to the patient an effective amount of polypeptide having epidermal growth factor activity so as to contact the blood deprived tissue therewith.

2. The method of claim 1, wherein the tissue is selected from the group consisting of neuronal tissue, myocardial tissue, lung tissue, spleen tissue, intestinal tissue or renal tissue.

3. The method of claim 1, wherein the polypeptide is epidermal growth factor.

4. The method of claim 1, wherein the contacting is achieved by intravenous administration of the polypeptide.

5. The method of claim 1, wherein a fibrinolytic agent is administered to the patient prior to or simultaneously with the administration of the polypeptide.

6. The method of claim 1, wherein a free radical scavenger material is administered to the patient Prior to or simultaneously with the administration of the polypeptide.

7. A method for preventing tissue damage in a patient resulting from the deprivation of blood supply to the tissue for a tissue damaging amount of time, comprising administering to the patient, prior to the blood supply deprivation to the tissue, an effective amount of a polypeptide having epidermal growth factor activity so as to contact the tissue therewith.

8. A method for preventing reperfusion injury to tissue in a patient after the tissue has suffered from ischemia, comprising administering to the patient a polypeptide having epidermal growth factor activity in a reperfusion injury Preventing amount so as to contact the tissue therewith.

9. A method for treating cerebrovascular disease in a patient resulting from an ischemic event, comprising administering to the patient an effective amount of a polypeptide having epidermal growth factor activity.

10. A method for preventing tissue damage in a patient after the tissue has been deprived of blood supply for a tissue damaging amount of time, comprising:
 a) administering to the patient a fibrinolytic agent, and followed by
 b) administering to the patient an effective amount of a polypeptide having epidermal growth factor activity.

* * * * *